US011284811B2

(12) United States Patent
Kawrykow et al.

(10) Patent No.: US 11,284,811 B2
(45) Date of Patent: Mar. 29, 2022

(54) MAGNETIC RESONANCE VOLUMETRIC IMAGING

(71) Applicant: ViewRay Technologies, Inc., Mountain View, CA (US)

(72) Inventors: Iwan Kawrykow, Sofia (BG); Georgi Gerganov, Sofia (BG); James F. Dempsey, Atherton, CA (US)

(73) Assignee: VIEWRAY TECHNOLOGIES, INC., Mountain View, CA (US)

( * ) Notice: Subject to any disclaimer, the term of this patent is extended or adjusted under 35 U.S.C. 154(b) by 780 days.

(21) Appl. No.: 15/628,255

(22) Filed: Jun. 20, 2017

(65) Prior Publication Data
US 2017/0367612 A1 Dec. 28, 2017

Related U.S. Application Data

(60) Provisional application No. 62/353,530, filed on Jun. 22, 2016.

(51) Int. Cl.
A61B 5/055 (2006.01)
A61B 5/00 (2006.01)
(Continued)

(52) U.S. Cl.
CPC ............ *A61B 5/055* (2013.01); *A61B 5/7257* (2013.01); *G01R 33/285* (2013.01);
(Continued)

(58) Field of Classification Search
CPC ......... A61B 5/05; A61B 5/055; A61B 5/7257; A61B 2090/374; A61B 90/37; G06T 7/74;
(Continued)

(56) References Cited

U.S. PATENT DOCUMENTS 6,005,916 A 12/1999 Johnson et al.
6,636,645 B1 10/2003 Yu et al.
(Continued)

FOREIGN PATENT DOCUMENTS

JP 2004509723 4/2004
JP 2006218315 8/2006
(Continued)

OTHER PUBLICATIONS von Siebenthal et al. "4D MR imaging of respiratory organ motion and its variability". Phys. Med. Biol. 52 (2007) 1547-1564 doi: 10.1088/0031-9155/52/6/001. (Year: 2007).*
(Continued)

*Primary Examiner* — Amanda Lauritzen Moher
*Assistant Examiner* — Delia M. Appiah Mensah
(74) *Attorney, Agent, or Firm* — Pillsbury Winthrop Shaw Pittman LLP

(57) ABSTRACT

Reference data relating to a portion of a patient anatomy during patient motion can be acquired from a magnetic resonance imaging system (MRI) to develop a patient motion library. During a time of interest, tracking data is acquired that can be related to the reference data. Partial volumetric data is acquired during the time of interest and at approximately the same time as the acquisition of the tracking data. A volumetric image of patient anatomy that represents a particular motion state can be constructed from the acquired partial volumetric data and acquired tracking data.

31 Claims, 9 Drawing Sheets

(51) Int. Cl.

| | | |
|---|---|---|
| *A61B 90/00* | (2016.01) | |
| *G01R 33/563* | (2006.01) | |
| *G06T 7/73* | (2017.01) | |
| *G01R 33/28* | (2006.01) | |
| *G01R 33/56* | (2006.01) | |
| *G01R 33/567* | (2006.01) | |
| *G01R 33/48* | (2006.01) | |
| *G01R 33/565* | (2006.01) | |

(52) U.S. Cl.
CPC .......... *G01R 33/56325* (2013.01); *G06T 7/74* (2017.01); *A61B 90/37* (2016.02); *A61B 2090/374* (2016.02); *G01R 33/4808* (2013.01); *G01R 33/4824* (2013.01); *G01R 33/5608* (2013.01); *G01R 33/5676* (2013.01); *G01R 33/56509* (2013.01)

(58) Field of Classification Search
CPC ............ G01R 33/56325; G01R 33/285; G01R 33/56509; G01R 33/4808; G01R 33/4824; G01R 33/5676; G01R 33/5608
See application file for complete search history.

(56) References Cited

U.S. PATENT DOCUMENTS

| | | | |
|---|---|---|---|
| 7,092,573 | B2 | 8/2006 | Luo et al. |
| 7,202,663 | B2 | 4/2007 | Huang |
| 7,230,429 | B1 | 6/2007 | Huang et al. |
| 7,265,545 | B2 | 9/2007 | Kruger et al. |
| 7,460,637 | B2 | 12/2008 | Clinthorne |
| 7,486,839 | B2 | 2/2009 | Moriguchi |
| 7,532,705 | B2 | 5/2009 | Yin |
| 7,542,622 | B1 | 6/2009 | Angelini et al. |
| 7,659,718 | B1 | 2/2010 | Lustig et al. |
| 7,791,338 | B2 | 9/2010 | Kim et al. |
| 7,840,045 | B2 | 11/2010 | Guo et al. |
| 8,155,417 | B2 | 4/2012 | Piron et al. |
| 8,310,233 | B2 | 11/2012 | Trzasko et al. |
| 9,472,000 | B2 | 10/2016 | Dempsey et al. |
| 2003/0068097 | A1 | 4/2003 | Wilson et al. |
| 2004/0054248 | A1 | 3/2004 | Kimchy et al. |
| 2005/0197564 | A1 | 9/2005 | Dempsey |
| 2005/0207531 | A1 | 9/2005 | Dempsey et al. |
| 2006/0033496 | A1 | 2/2006 | Shvartsman |
| 2006/0079754 | A1* | 4/2006 | Welch ................ G01R 33/4824 600/410 |
| 2006/0120583 | A1 | 6/2006 | Dewaele |
| 2007/0083114 | A1 | 4/2007 | Yang et al. |
| 2007/0159174 | A1 | 7/2007 | Oshio |
| 2007/0230770 | A1 | 10/2007 | Kulkarni et al. |
| 2008/0197842 | A1 | 8/2008 | Lustig et al. |
| 2009/0039886 | A1 | 2/2009 | White |
| 2009/0240135 | A1 | 9/2009 | Gleich |
| 2010/0312100 | A1 | 12/2010 | Zarkh et al. |
| 2010/0322497 | A1 | 12/2010 | Dempsey et al. |
| 2011/0285960 | A1 | 11/2011 | Kohn |
| 2012/0165652 | A1 | 6/2012 | Dempsey |
| 2012/0197102 | A1 | 8/2012 | Hanebuchi |
| 2012/0245453 | A1 | 9/2012 | Tryggestad |
| 2013/0261429 | A1 | 10/2013 | Lee et al. |
| 2013/0345545 | A1 | 12/2013 | Gross et al. |
| 2015/0126850 | A1 | 5/2015 | Cetingul |
| 2015/0346304 | A1 | 12/2015 | Hu |
| 2016/0232690 | A1 | 8/2016 | Ahmad |
| 2016/0252596 | A1 | 9/2016 | Nielsen |
| 2016/0324500 | A1* | 11/2016 | Fan .................... G01R 33/5676 |
| 2016/0324664 | A1 | 11/2016 | Piron |
| 2016/0334479 | A1 | 11/2016 | Poole |
| 2017/0032544 | A1 | 2/2017 | Dempsey |

FOREIGN PATENT DOCUMENTS

| | | |
|---|---|---|
| JP | 2011041656 | 3/2011 |
| JP | 2012029767 | 2/2012 |
| JP | 2013190421 | 9/2013 |
| JP | 2016516508 | 6/2016 |
| WO | WO-2003/008986 A2 | 1/2003 |
| WO | 2010143400 | 12/2010 |
| WO | 2015138945 | 9/2015 |

OTHER PUBLICATIONS

Buerger et al. "3D Non-Rigid Motion Modeling of the Liver from Undersampled Golden-Radial Phase Encoding (G-RPE) Acquisitions". Proc. Intl. Soc. Mag. Reson. Med. 19 (2011). p. 643. (Year: 2011).*

Kim et al. "Extraction of Cardiac and Respiratory Motion Cycles by Use of Projection Data and Its Applications to NMR Imaging". Magnetic Resonance in Medicine 13,25-37 (1990). (Year: 1990).*

Krombach G.A. "MRI Guidance of Vascular Applications". In: Kahn T., Busse H. (eds) Interventional Magnetic Resonance Imaging. Medical Radiology. Springer, Berlin, Heidelberg. (2011) (Year: 2011).*

Bhat et al. "3D Radial Sampling and 3D Affine Transform-based Respiratory Motion Correction Technique for Free-breathing Whole-Heart Coronary MRA with 100% Imaging Efficiency". Magn Reson Med. May 2011; 65(5): 1269-1277. doi:10.1002/mrm.22717. (Year: 2011).*

Lin et al. "Heart deformation analysis: measuring regional myocardial velocity with MR imaging". Int J Cardiovasc Imaging (2016) 32:1103-1111. DOI 10.1007/s10554-016-0879-z (Year: 2016).*

Crijns et al. "Proof of concept of MRI-guided tracked radiation delivery: tracking one-dimensional motion". Phys. Med. Biol. 57 (2012) 7863-7872 doi:10.1088/0031-9155/57/23/7863 (Year: 2012).*

Barth, et al. "Simultaneous Multislice (SMS) Imaging Techniques." Magnetic Resonance in Medicine; vol. 75; pp. 63-81; 2016.

Kolbitsch, C. et al; "Cardiac Function Asssesment Without ECG Using Image-based Navigation"; Proceeding of the International Society for Magnetic Resonance in Medincine, 20th Annual Meeting & Exhibition; May 5, 2010; p. 3849; KP040626270; Maelbourne, Australia.

Kolbitsch, C. et al; "Image-based Self-navigator Using Cardiac Functional Parameters for Cine Imaging"; Proceeding of the International Society for Magnetic Resonance in Medincine, 20th Annual Meeting & Exhibition; May 5, 2010; p. 602; KP040623030; Maelbourne, Australia.

Paganelli Chiara et al; Liver 4DMRI: A Retrospective Image-based Sorting Method, Medical Physics, AIP; Melville, NY, US; vol. 42; No. 8; Jul. 24, 2015; pp. 4814-4821; XP012199252; ISSN: 0094-2405; DOI: 10.1118/1.4927252 (Retrieved on Jan. 1, 1901); Section 2.B.

PCT App. No. PCT/US2017/038520; International Search Report and Written Opinion dated Oct. 4, 2017.

Smolikova, R. et al.; "Registration of Fast Cine Cardiac MR Slices to 3D Procedural Images: Toward Real Time Registration for MRI-guided Procedures"; Proceedings of SPIE, Medical Imaging 2004; vol. 5370 II; Feb. 16, 2004; pp. 1195-1205; XP040181910; San Diego, CA.

Von, Siebenthal M. et al; "4D MR Imaging of Respiratory Organ Motion and its Variability; 4D MRI of Respiratory Organ Motion", Physics in Medicine and Biology, Instititue of Physics Publishing, Bristol GB, vol. 52, No. 6, Mar. 21, 2007, pp. 1547-1564, XP20113239, ISSN: 0031-9155, DOI: 10.1088/0031-9155/52/6/001, pp. 1547-1553.

Yoon et al. ("Accuracy of an Automatic Patient-Positioning System Basedon the Correlation of Two Edge Images in Radiotherapy",Journal of Digital Imaging, vol. 24, No. 2 (Apr. 2011): pp. 322-330).

PCT App. No. PCT/US2017/038520; International Preliminary Reporton Patentability dated Jan. 3, 2019; (pp. 1-10).

Corrected Notice of Allowability dated Apr. 4, 2018 for U.S. Appl. No. 14/559,880 (pp. 1-4).

Notice of Allowance dated Mar. 19, 2018 for U.S. Appl. No. 14/559,880 (pp. 1-7).

Office Action dated Dec. 6, 2017 for U.S. Appl. No. 15/294,533 (pp. 1-7).

(56) References Cited

OTHER PUBLICATIONS

Notice of Allowance dated Apr. 19, 2018 for U.S. Appl. No. 15/294,533 (pp. 1-8).
Office Action dated Jun. 27, 2019 for U.S. Appl. No. 15/630,890 (pp. 1-7).
Bilgin, A. et al. "Randomly Perturbed Radial Trajectories for Compressed Sensing MRI." *Proceedings of International Society for Magnetic Resonance in Medicine*.16 (2008):3152.
Blaimer, et al. "Smash, Sense, Pills, Grappa, How to Choose the Optimal Method" Top Magan Reson Imaging, vol. 1515, No. 4, Aug. 2004.
Candes, et al. "Robust Uncertainty Principles: Exact Signal Reconstruction from Highly Incomplete Frequency Information." IEEE Transactions on Information Theory, vol. 52, No. 2, Feb. 2006.
Candes, et al. "Sparsity and Incoherence in Compressive Sampling" Nov. 2006.
CIPRA "l1-magic" from SIAM News, vol. 39, No. 9, Nov. 2006.
Donoho, "Compressed Sensing" Sep. 14, 2004.
Foroosh, Hassan, et.al. "Extension of Phase Correlation to Subpixel Registration." *IEEE Transactions on Image Processing*, vol. 11, No. 3, 2002, pp. 188-200.
Greganov, G, et al. "Portal Image Registration Using the Phase Correlation Method." *IEEE Nuclear Science Symposium and Medical Imaging Conference*, 2013. pp. 1-3. [retrieved on Jun. 10, 2014].
Haacke E M et al. "Constrained reconstruction: A superresolution, optimal signal-to-noise alternative to the Fourier transform in magnetic resonance imaging." Medical Physics, AIP, Melville, NY, US, vol. 16, No. 3, May 1, 1989 (May 1, 1989), pp. 388-397, XP000034068, ISSN: 0094-2405, DOI: 10.1118/1.596427.
Hernando, D. et al. "Interventional MRI with sparse sampling: an application of compressed sensing." *Proceedings of International Society for Magnetic Resonance in Medicine*.16 (2008):1482.
International Search Report for corresponding PCT/US10/39036 dated Aug. 11, 2010.
Irarrazabal, et al. "Fast Three Dimensional Magnetic Resonance Imaging."
Lagendijk J. J. et al. "MRI guided radiotherapy: A MRI based linear accelerator." Radiotherapy & Oncology. vol. 56, No. Supplement 1. Sep. 2000. (Sep. 2000):S60-S61. XP008012866. 19th Annual Meeting of the European Society for Therapeutic Radiology and Oncology. Istanbul, Turkey, Sep. 19-23, 2000.
Law, C. , and Glover, G. "Deconvolving Haemodynamic Response Function in fMRI under high noise by Compressive Sampling." *Proceedings of International Society for Magnetic Resonance in Medicine*. 17 (2009):1712.
Li, Kang and Kanadae, Takeo. "Nonnegative Mixed-Norm Preconditioning for Microscopy Image Segmentation." *Information Processing in Medical Imaging*. Springer Berlin Heidelberg.vol. 5636. (2009):362-373.
Lustig et al. (2005) (Faster Imaging with Randomly Perturbed, Undersampled Spirals and |L|.sub.—1 Reconstruction, Proceedings of the 13th Annual Meeting of ISMRM, Miami Beach).
Lustig, et al. "L1 SPIR-IT: Autocalibrating Parallel Imaging Compressed Sensing."
Meyer, et al. "Fast Spiral Coronary Artery Imaging", Magnetic Resonance in Medicine 28, pp. 202-213 (1992).
Reddy, B. Srinivas, and B. N. Chatterji. "An FFT-Based Technique for Translation, Rotation, and Scale-Invariant Image Registration." *IEEE Transactions on Image Processing*, vol. 5, No. 8, 1996, pp. 1266-1271.
Riek, et al. "Flow Compensation in MRI Using a Phase-Corrected Real Reconstruction", 1993.
Roullot E et al. "Regularized reconstruction of 3D high-resolution magnetic resonance images from acquisitions of anisotropically degraded resolutions." Pattern Recognition, 2000. Proceedings. 15th International Conference on Sep. 3-7, 2000; [Proceedings of the International Conference on Pattern Recognition. (ICPR)], Los Alamitos, CA, USA,IEEE Comput. Soc, US, vol. 3, Sep. 3, 2000 (Sep. 3, 2000), pp. 346-349.
Tamada and Kose. "Two-Dimensional Compressed Sensing Using the Cross-sampling Approach for Low-Field MRI Systems." IEEE Transactions on Medical Imaging. vol. 33, No. 9. Sep. 2004. pp. 1905-1912.
Trzasko et al. "Highly Undersampled Magnetic Resonance Image Reconstruction via Homotopic 10—Minimization" IEEE Transactions on Medical Imaging.
Yang, et al. "A Fast TVL1-L2 Minimization Algorithm for Signal Reconstruction from Partial Fourier Data."
Zitova, Barbara, and Jan Flusser."Image Registration Methods: A Survey." *Image and Vision Computing*, vol. 21, 2003, pp. 977-100.
Yuichiro Tajima, et al., "A Study on Non-Rigid Volume Registration Using 3D Phase-Only Correlation," Technical Report of the Institute of Electronics, Information and Communication Engineers, Japan, IEICE, May 10, 2012, vol. 112, No. 38, pp. 107-112.

\* cited by examiner

MAGNETIC RESONANCE VOLUMETRIC IMAGING

CROSS-REFERENCE TO RELATED APPLICATION

This application claims the benefit of priority under 35 U.S.C. 119 of U.S. Provisional Application No. 62/353,530, filed Jun. 22, 2016, entitled "MAGNETIC RESONANCE VOLUMETRIC IMAGING". The disclosure of which is incorporated herein by reference in its entirety.

TECHNICAL FIELD

The subject matter described herein relates to systems, methods and computer programs for magnetic resonance data acquisition and image reconstruction.

BACKGROUND

Three-dimensional, or volumetric, imaging of a patient with a magnetic-resonance imaging system can provide valuable information for patient diagnosis and treatment. It can also be valuable to have the benefit of volumetric image sequences depicting the movement of patient tissues over time. Such may be referred to in the art as 4-D MRI, cine MRI or sometimes real-time MRI.

SUMMARY

In one aspect, reference data relating to a portion of a patient anatomy during patient motion is acquired from a magnetic resonance imaging system (MRI) to develop a patient motion library. During a time of interest, tracking data is acquired that can be related to the reference data. Partial volumetric data is acquired during the time of interest and at approximately the same time as the acquisition of the tracking data. A volumetric image of patient anatomy that represents a particular motion state may be constructed from the acquired partial volumetric data and acquired tracking data.

In some variations, one or more of the following features can optionally be included in any feasible combination.

Reference data can be an integrated projection through the portion of the patient anatomy. The integrated projection can be transformed to planar k-space data based on an angle between the patient anatomy and the MRI system.

Tracking data can correspond to a subset of radial k-space data that can be used to reconstruct the portion of the patient anatomy corresponding to a closest match of the tracking data with the reference data.

Tracking data and the partial volumetric data can be acquired in direct sequence. The acquiring of the tracking data can include replacing a corresponding radial line in previously acquired radial k-space data where the tracking data is acquired along a single radial line in k-space. The reference data, tracking data, and partial volumetric data can be k-space data or planar image data. The partial volumetric data can be correlated with the tracking data.

Tracking data can be related to the reference data comprising by deforming, with digital interpolation, extrapolation, or translation, the reference data to improve a goodness-of-fit metric that describes the quality of the relating of the tracking data to the reference data. The deforming can be further based on a velocity of patient motion measured from the tracking data.

Partial volumetric data can be acquired according to a predefined sequence of k-space regions or can correspond to a k-space region from the predefined sequence that has not already been acquired. Partial volumetric data can be planar data corresponding to planes in the portion of the patient anatomy.

Partial volumetric data can be acquired immediately after the acquiring of the tracking data. Also, the acquiring of tracking data and partial volumetric data can be continuous and alternating between the acquisition of tracking data and partial volumetric data.

At least some of the tracking data or the partial volumetric data can be added to the patient motion library. Tracking data can be planar k-space data or three-dimensional k-space data.

Volumetric images can be constructed and combined to generate a time-resolved volumetric image sequence. The constructing of volumetric images can include partitioning the patient motion library into motion states, each of the motion states corresponding to a portion of the patient motion. Also, determining the motion state corresponding to the tracking data by finding the closest match between the tracking data and the reference data. Based on the determined motion state, the partial volumetric data acquired during one of the plurality of motion states can be added to a volumetric data set corresponding to the one of the motion states, the constructed volumetric image comprising a complete set of partial volumetric data.

Radiation treatment can be delivered to a patient based at least on the tracking data. Also, the time of interest can be during delivery of radiation treatment to a patient. The time of interest can be during a period of diagnostic observation. The acquiring of the reference data can occur before delivering radiation treatment to the patient. The acquiring of the reference data can occur after delivering radiation treatment to the patient.

In an interrelated aspect, tracking data from at least one plane intersecting the patient and partial volumetric data of a volume of interest of a patient can be acquired during patient treatment.

In some variations, one or more of the following features can optionally be included in any feasible combination. Tracking data and the partial volumetric data can be acquired in an alternating fashion. Tracking data can be 2-D radial k-space data corresponding to the at least one plane. A motion phase of a patient can be identified based on comparing the tracking data to reference data that describes a region of a patient exhibiting a number of motions.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a computer-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to a system for generating volumetric images from partial MRI image data, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
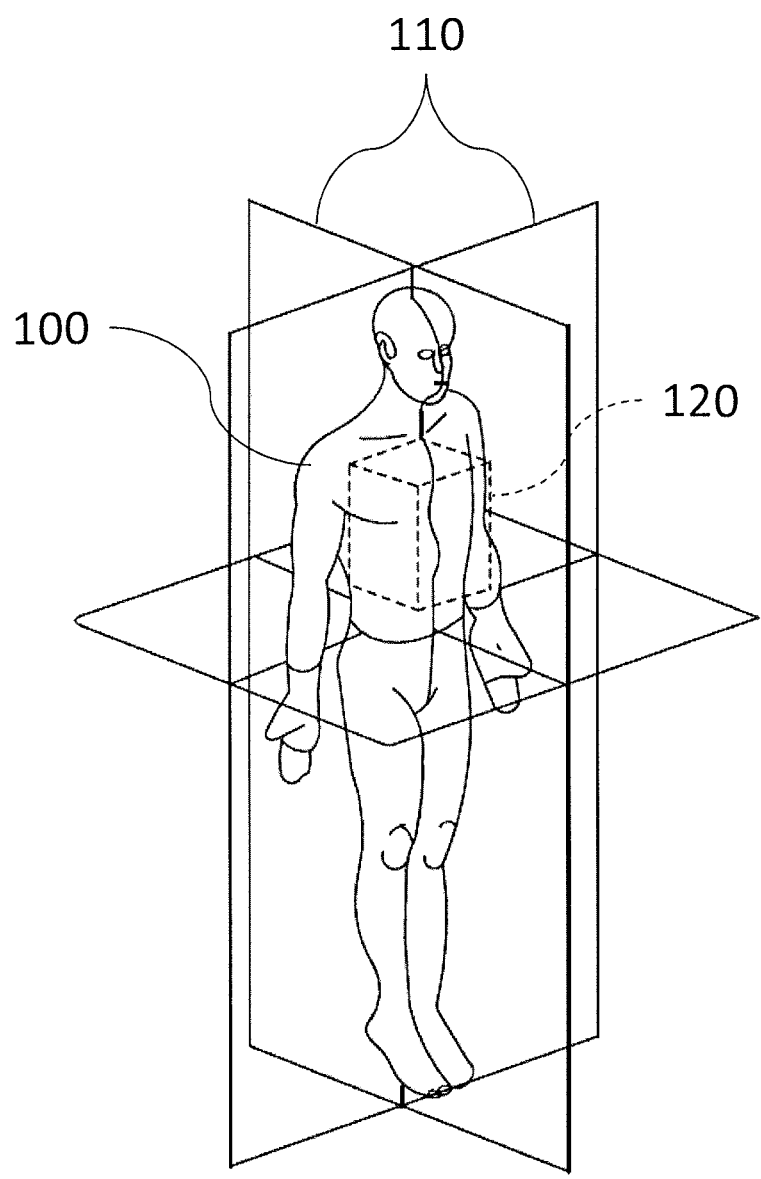
FIG. 1 is a diagram illustrating a patient intersected by imaging planes and a volume of interest.

FIG. 1 is a diagram illustrating a patient 100 intersected by imaging planes 110 and including a volume of interest 120. Magnetic Resonance Imaging (MRI) can provide navigator (1-D), planar (2-D) or volumetric (3-D) images of patient 100.

Three-dimensional images of patient anatomy (organs, tumors, etc.) in volume of interest 120 may be taken over a time of interest (for example, during a patient treatment) and can be combined to generate a time-resolved volumetric image sequence showing movement of patient anatomy (e.g., movement may occur as a result of a heartbeat, the digestive process, breathing, etc.). Ideally, real-time volumetric imaging of patient anatomy would be generated and displayed during the particular time of interest (for example, during MRI-assisted diagnostics or during patient therapy). Alternatively, according to one implementation of the present disclosure, partial data may be acquired during the time of interest and the volumetric images reconstructed afterwards. Assuming that patient 100 is in motion during the time of interest, the partial volumetric data acquired can correspond to different positions (or motion states) of patient 100.

To assist with the sorting of acquired partial volumetric data into motion states, an image of a single planar region of a patient 100 may be acquired at approximately the same time as the acquisition of the partial volumetric data to provide valuable tracking data. The planar image can then be compared with a library of planar images of patient 100 documenting patient motion (e.g., lying on a treatment couch, breathing normally). From the comparison, a particular state of patient motion can be identified. Acquisitions of partial volumetric data sets that correspond to the same motion state can then be combined to provide a complete (or substantially complete) volumetric data set for the volume of interest during that motion state. Time-resolved volumetric image sequences can be generated by sequencing the complete volumetric data sets according to the patient motion states exhibited over time, as indicated by the tracking data.

The time-resolved volumetric image sequences generated by the systems, methods and software described herein may be referred to as 4-D MRI, cine MRI, real-time MRI and the like. Such sequences may be used in patient diagnoses that will benefit from a depiction of 3-D motion over time. Such cine MRI may also be used in interventional applications, for example, in providing a 4-D depiction of patient movement along with the movement of a surgical tool during a procedure.

In another application, time-resolved volumetric image sequences are used to enhance radiation therapy treatment. As one example, the knowledge of the locations of a patient's tissues while a radiation beam is aimed at the patient allows for an accurate calculation of the radiation dose received by the patient's tissues during the treatment. Further benefits with respect to radiation therapy treatment are discussed below. While the terms treatment, treatment images, treatment time and the like are used herein, the present disclosure contemplates its imaging technology being used during any time of interest, whether it be during a particular type of treatment, diagnostic procedure, or any other procedure where the technology proves beneficial.

Figure 2:
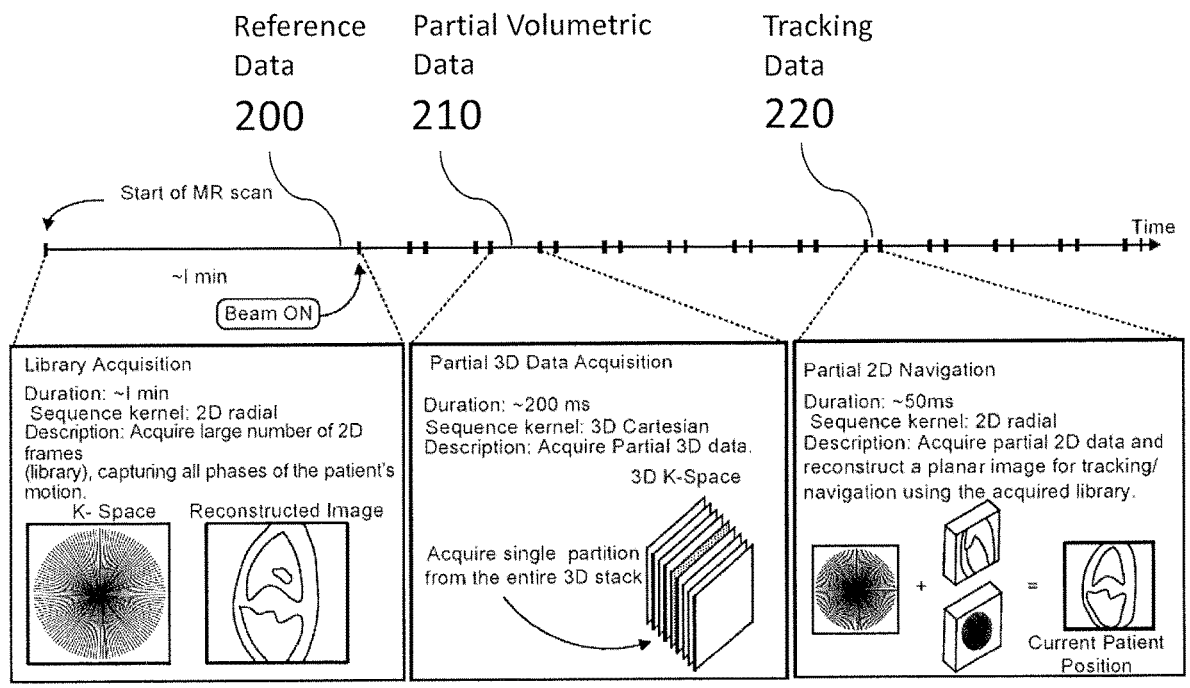
FIG. 2 is a diagram illustrating an example of a sequence for acquiring reference data, partial volumetric data, and tracking data.

FIG. 2 is a diagram illustrating a sequence of acquiring reference data 200, partial volumetric data 210, and tracking data 220.

The example timeline shown in FIG. 2 begins with acquisition of reference data 200 that is stored in a patient motion library. The present disclosure contemplates the acquisition of reference data 200 occurring at other times as well, for example, after the acquisition of volumetric data and before, during or after a particular time of interest. Reference data 200 can be used to define motion states of the patient anatomy. In one example where patient 100 is receiving radiation therapy, the patient may be asked to breathe deeply during the acquisition of reference data 200 to provide a broad range of motions the patient may move through during a treatment. If the patient's neck is being treated, he or she may be asked to move their head, talk, or swallow during the acquisition of reference data 200.

As shown in the example timeline, after reference data 200 is acquired, alternating acquisition periods of partial volumetric data 210 and tracking data 220 can occur. The patient motion library can be data stored in persistent memory located at, for example, a remote server, a computer controlling patient treatment, the MRI system, etc.

During a time of interest, for example, during radiation treatment of a patient 100, or during a period of diagnostic observation, tracking data 220 can be acquired and related to reference data 200. In an exemplary method, partial volumetric data 210 can be acquired during the time of interest and at approximately the same time as the acquisition of tracking data 220. As used herein, "approximately the same time" means that tracking data 220 and partial volumetric data 210 are either acquired in direct sequence (i.e., one immediately after the other), with small gaps between the two types of acquisition, or at overlapping times where feasible. The primary constraint is that the gaps, if any, are sufficiently small to allow tracking data 220 to be acquired when the patient anatomy is in approximately the same position, orientation, and shape as when partial volumetric data 210 is acquired so that the partial volumetric data 210 can be correlated with tracking data 220. Another constraint can be that tracking data 220 and partial volumetric data 210 are each acquired predominantly during a single motion state.

In some implementations, as illustrated in FIG. 2, the acquisition of tracking data 220 and partial volumetric data 210 is continuous and alternating between the acquisition of tracking data 220 and the acquisition of partial volumetric data 210. As shown in the example of FIG. 2, tracking data 220 is acquired in 50 ms intervals interleaved with 200 ms intervals of acquiring partial volumetric data 210. In other exemplary implementations, tracking data 220 may be acquired over 5, 10, 25, or 100 ms intervals. Similarly, partial volumetric data 210 can, in other implementations, be acquired over 10, 50, 100, 300, 400, or 500 ms intervals.

The alternating pattern of acquiring tracking data 220 and partial volumetric data 210 can allow partial volumetric data 210 to be related to neighboring portions of tracking data 220. Tracking data 220 can thus be compared to reference data 200 to relate the partial volumetric data 210 to the reference data 200. In a specific example, by identifying reference data 200 that tracking data 220 corresponds to, the partial volumetric data 210 can be binned into a particular motion state defined in the patient motion library. When enough partial volumetric data 210 is acquired to make a complete, or nearly complete, volumetric data set, a three-dimensional image of the patient anatomy during that motion state can be reconstructed. Details of the acquisition of reference data 200, tracking data 220, and partial volumetric data 210 are further described below.

Figure 3:
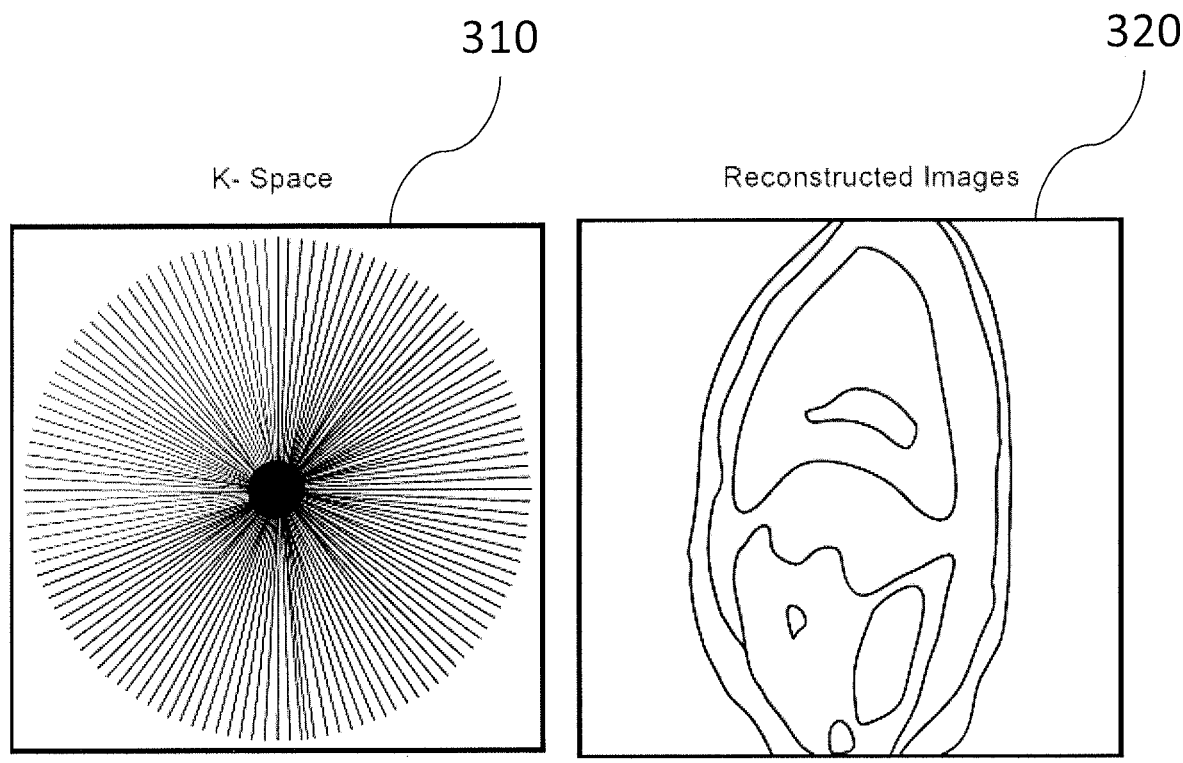
FIG. 3 is a diagram illustrating planar k-space data and a planar image.

FIG. 3 is a diagram illustrating planar k-space data 310 used to generate planar images 320. An MRI system can acquire reference data 200 relating to a portion of a patient anatomy during patient motion. Reference data 200 can then be used to develop a patient motion library that describes motion states of a patient 100. The reference data 200 can be, for example, any type of k-space data (e.g., 1-D, 2-D, 3-D), projection data, planar image data, volumetric data, combinations of such, etc. Reference data 200 can be taken along one or more integrated projections through a portion of the patient anatomy. The projection can include a planar section (see also FIG. 1) intersecting part of a patient's anatomy, for example, the heart, lung, kidneys, etc. The integrated projection can be transformed to planar k-space data 310 based on the angle between the patient anatomy and the MRI system. In some implementations, a plane used for reference data 200 can be separated from any volumes corresponding to the partial volumetric data 210.

The radial pattern for the planar k-space data 310 shown in FIG. 3 represents one example pattern for imaging a k-space region. The sequence of radial acquisition can be according to a cyclical ordering scheme, for example, a cycle 4, cycle 8, etc. Other radial acquisition options can include, for example, golden angle ratio, bit-reversed (0, 4, 6, 1, 5, 3, 7), random, interleaved-taking lines that are nearby or adjacent in angle, such as lines 0-1, 5-6, 10-11, for a radial distribution of k-space lines. When a sufficient k-space data set is acquired, a planar image 320 can be reconstructed by an inverse Fourier transform. The planar image 320 can then be stored in a patient motion library.

Reference data 200, tracking data 220, planar images 320 (e.g., reconstructed with tracking data 220 or reference data 200), and/or partial volumetric data 210 can be added to the patient motion library at any time, for example, before delivering a radiation treatment, during a radiation treatment, or after delivering a radiation treatment. The quality of a patient motion library can be continuously improved by adding reference data 200 from previous time periods or from other patients. The addition of reference data 200 can also allow averaging over previous measurements to improve image resolution and remove noise. In some implementations, a simple average can be performed across a subset of reference data 200. In other implementations, the averaging can include more sophisticated techniques such as weighting based on the time the reference data 200 was acquired, the patient anatomy imaged, correlation with prior reference data to determine a degree of similarity of the reference data 200, etc. Including additional reference data 200 can also expand the number of usable motion states in the same manner as that described above.

In yet another implementation, the partial volumetric data, tracking data, volumetric images, planar images 320, or any of the reference data 200 stored in the patient motion library can be manipulated or modified to provide additional reference data 200 for a range of patient motion outside that for which the reference data 200 was acquired. As one example, during reference data acquisition, a tumor or other portion of the patient anatomy may be recorded as moving within a 5 cm range in some direction. However, during treatment, the tumor may be observed to move within a 6 cm range. Instead of not attempting to match the imaged motion of the patient anatomy, the system can identify that the tumor has gone out of bounds of the reference data 200. Additional (or synthetic) reference data can be generated that translates the tumor to reach, or nearly so, the present tumor location. The additional reference data can be defined as an additional motion state. To generate additional reference data, the existing reference data 200 can be interpolated, extrapolated, or modified with deformable image registration, to correspond to other shapes or conditions of the patient anatomy.

Figure 4:
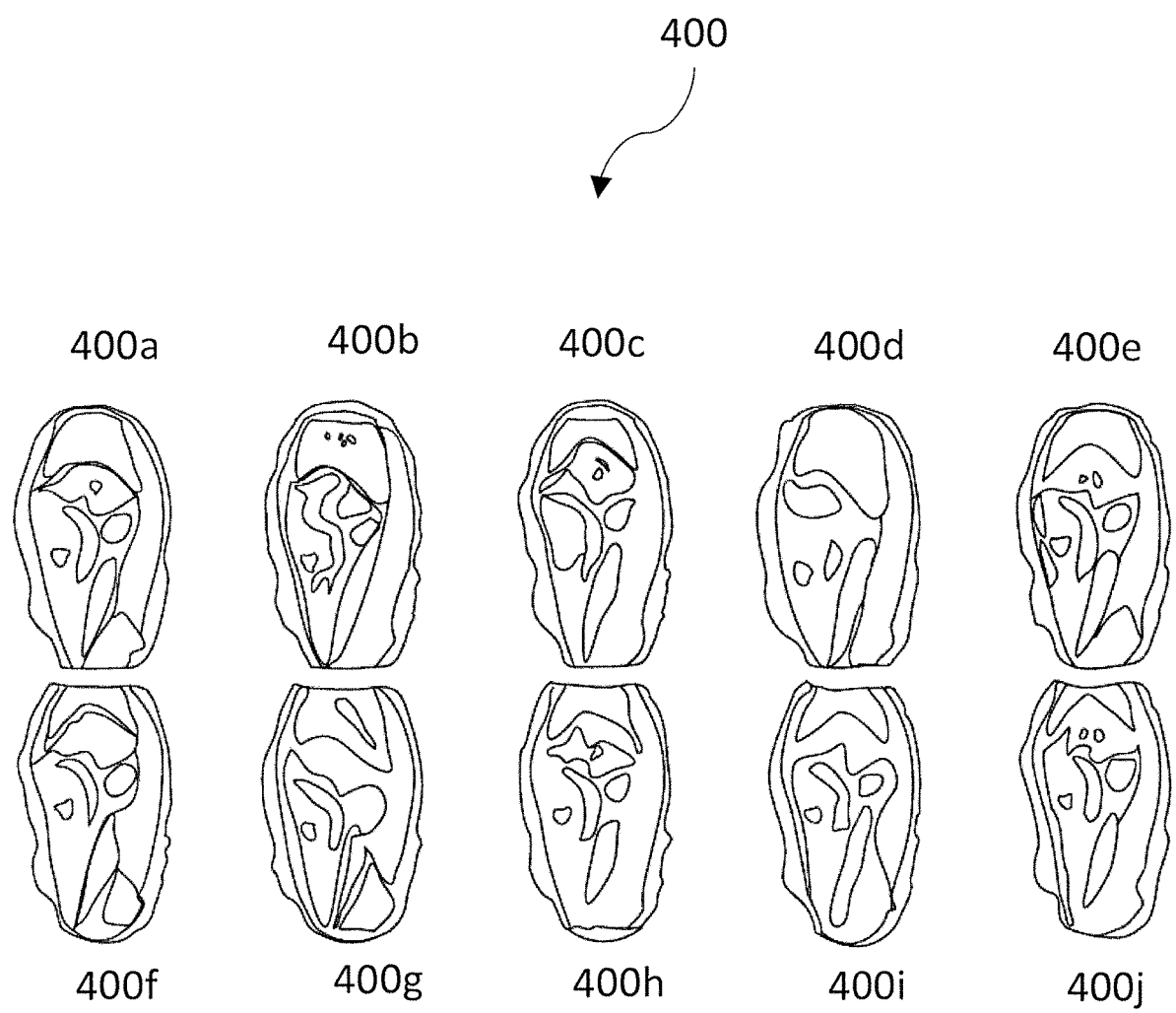
FIG. 4 is a diagram illustrating an example of the clustering of reference data into motion states.

FIG. 4 is a diagram illustrating clustering of reference data 200 into motion states 400(a-j). Reference data 200 can capture images of patient anatomy in a number of motion states 400. Any imaged motion, for example, a cycle of breathing, can be divided into an arbitrary number of motion states 400. For example, one cycle of patient breathing can be divided into 10 or 15 motion states 400 that correspond to a full inhale and exhale. There are 10 motion states 400(a-j) shown in the example shown in FIG. 4. Also, motion states 400 can be composites of different types of patient motion. For example, the position of a tumor near the heart can be affected not only by the motion of patient 100 breathing, but also by the contractions and expansions of the heart. In this example, a set of motion states 400 can include any combination of motions due to the movement of the heart and lungs.

Reference data 200 can be partitioned into the specified number of motion states 400. The partitioning can be performed by an algorithm that employs pattern-matching, ranking, or clustering. The example below describes one implementation of a clustering algorithm. In one implementation, each planar image 320 in the patient motion library can be defined to consist of a point in an N-dimensional space, where N is the number of pixels in the reconstructed planar image 320. The distances between the points can be expressed as a Euclidean distance or as a function of a cross-correlation coefficient (CC). One example of such a distance function is (1-CC). Here, if CC was 1, this would indicate a zero distance between the two planar images (i.e., they are the same image). Initially, patient motion library can be searched for the two planar images that are the furthest apart (most different). Once found, these two planar images can be assigned to two different clusters. Then, each remaining planar image can be assigned to the nearest of the two clusters. At this point there are two motion states defined for the patient motion library. To generate additional motion states, the cluster with the largest variation can be identified. The identification can be performed by determining the variation in distances of the planar images 320 in the cluster from the center of the cluster. Once the cluster with the largest variation is identified, planar images 320 in that cluster can be separated into two additional clusters in the same manner as described above. The process can continue until the number of clusters is the same as the predefined number of motion states 400.

Figure 5:
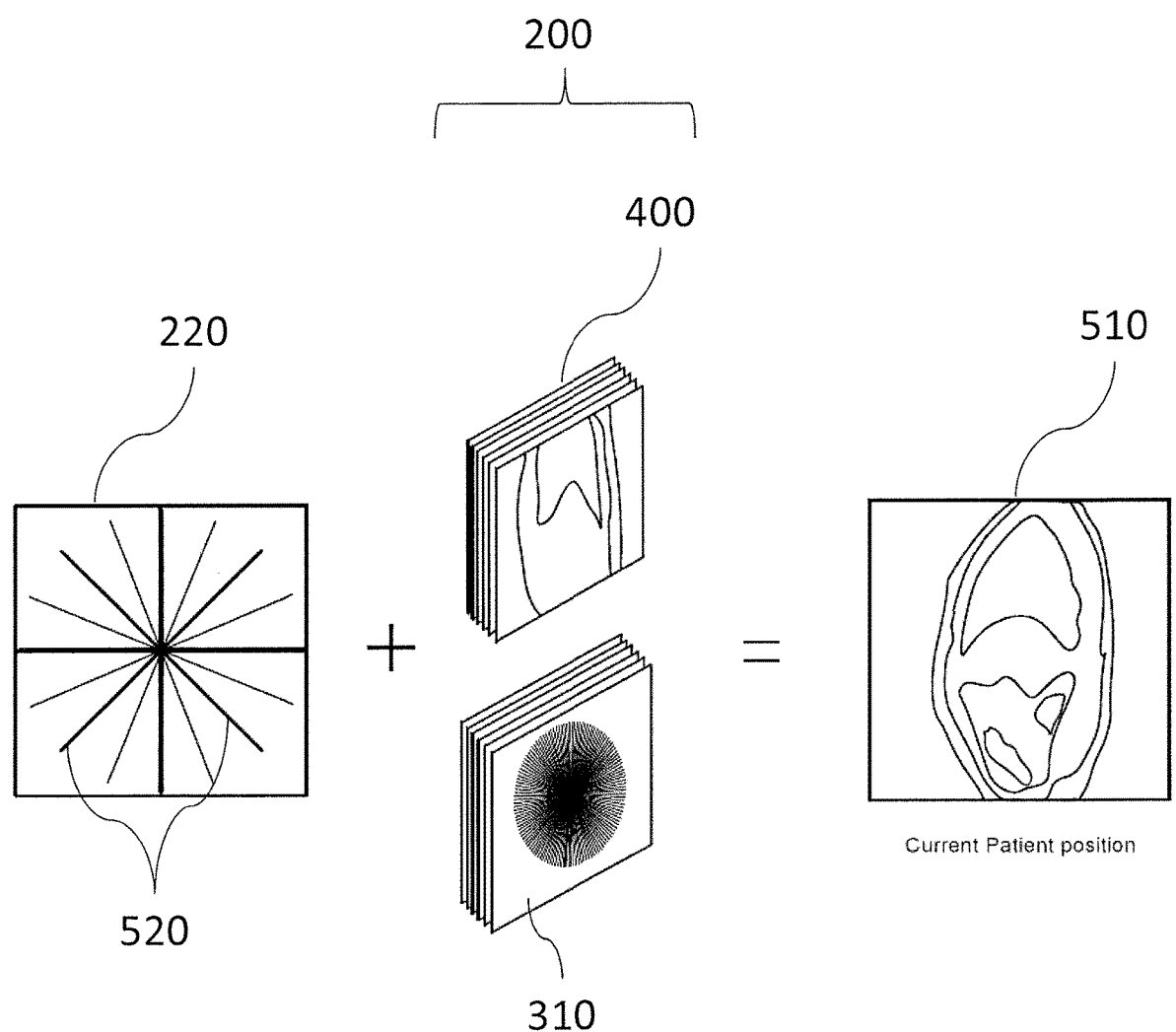
FIG. 5 is a diagram illustrating an exemplary concept for determining a patient motion state from tracking data and reference data.

FIG. 5 is a diagram illustrating an exemplary manner for determining a current patient motion state 510 from tracking data 220 and reference data 200. Tracking data 220 can be used, for example, not to reconstruct a planar image corresponding to the current motion state, but instead for a comparison with reference data 200, associated with motion states 400, which reference data may be in the form of planar k-space data 310. Based on the comparison, a current patient motion state 510 can be determined, for example, as described below.

In one implementation, planar k-space data 310 can be acquired as tracking data 220 that corresponds to, for example, one of the planes shown in FIG. 1. The tracking plane can also be selected to intersect a portion of the patient anatomy that is of interest for a treatment. For example, during treatment of a tumor in the lung of patient 100, a sagittal plane through the tumor may be used for tracking. In other implementations, the tracking data 220 can include, for example, any type of k-space data (e.g., 1-D, 2-D, 3-D), projection data, planar image data, volumetric data, combinations of such, etc. Three-dimensional k-space tracking data 220 can be of the same volume as the partial volumetric data 210 or of a different volume. In some implementations, the tracking plane can be a fixed plane through the patient anatomy that can generally correspond to the location at which the reference data 200 was acquired. The present disclosure contemplates any type of tracking data 220 that can be related to the chosen type of reference data 200.

In some implementations, reference data 200 can be a full 2-D data set (such as radial k-space data) that allows reconstruction of a planar image of a portion of patient anatomy. However, tracking data 220 can instead be a subset of radial k-space data. For example, when reference data 200 and tracking data 220 are 2-D radial k-space data, tracking data 220 can include fewer radial lines than the full k-space data sets in the reference data 200. In other implementations, tracking data 220 can span only a portion of the angular distribution in k-space that reference data 200 spans. The subset of k-space data, also referred to herein as matching lines 520 (shown as heavier lines in FIG. 5) in the tracking data 220 (shown sparsely for illustrative purposes) can be matched to their corresponding lines in reference data 200. The matching can include, for example, searching for a linear combination of k-space lines in reference data 200 that is a closest match to the lines in tracking data 220. In another implementation, the relating or correlating of tracking data 220 to reference data 200 can include deforming, by interpolation, extrapolation, or translation, reference data 200 to improve a goodness-of-fit metric that describes the quality of the relating of tracking data 220 to reference data 200. Lines from planar k-space data 310 in reference data 200 can be added to matching lines 520 to fill in missing lines. A planar image of the patient anatomy corresponding to the current patient motion state 510 can then be reconstructed from the combined reference data 200 and tracking data 220. Optionally, additional similar images from the patient motion library can be blended with the reconstructed image to improve final image quality.

In one implementation, planar images 320 can be constructed by the procedure detailed below. Step 1—Find k-space datasets in the patient motion library that have the highest cross-correlation with the measured matching lines 520. Step 2—Find the linear combination of k-space datasets that best fits the measured matching lines 520. Step 3—Fill in the missing k-space data by using the linear combination of coefficients found in Step 2.

Notation

M—Number of matching lines.

N—Total number of lines in the radial sampling pattern.

C—Number of channels/coils.

P—Number of points per radial line.

$K_{lib}$—Total number of full k-space datasets available in the patient motion library.

$l_1, l_2, \ldots l_N$—Line indices of the lines in the sampling pattern according to the used ordering scheme.

$\vec{m}_i^j$—Measured/restored complex data for the i-th line in the j-th channel for the current planar frame.

$\vec{k}_{d,i}^j$—Complex k-space data in the patient motion library for the i-th line in the j-th channel in the d-th dataset.

$$CC(\vec{a}, \vec{b}) = \frac{\sum_i (a_i - \bar{a})(b_i - \bar{b})}{\sqrt{\sum_i (a_i - \bar{a})^2 \sum_i (b_i - \bar{b})^2}}$$

Cross correlation coefficient between the vectors $\vec{a}$ and $\vec{b}$. The vectors have the same length and the summations are over all elements. $\bar{a}$ and $\bar{b}$ are averages of the vector elements $a_i$ and $b_i$.

Step 1 Details

To perform this step, the cross-correlation coefficients can be calculated between the measured matching lines 520 and each k-space dataset in the patient motion library. The k-space datasets with the largest CC can then be selected.

$$\vec{m}=(\vec{m}_{l1},\vec{m}_{l2},\ldots,\vec{m}_{lM}), \vec{m}_{li}=(\vec{m}_{li}^1,\vec{m}_{li}^2,\ldots,\vec{m}_{li}^C)$$

$$\vec{k}_{d,li}=(\vec{k}_{d,li}^1,\vec{k}_{d,li}^2,\ldots,\vec{k}_{d,li}^C)$$

$$\vec{k}_d=(\vec{k}_{d,l1},\vec{k}_{d,l2},\ldots,\vec{k}_{d,lM})$$

The $K_{lib}$ CC coefficients can then be calculated as $$CC_d=CC(\vec{k}_d,\vec{m}), d=1\ldots K_{lib}$$

In some implementations, $K_{lib}=10$. Indices of the k-space datasets with the largest CC coefficient are denoted by $d_1$, $d_2, \ldots, d_K$.

Step 2 Details

A search can be performed for a linear combination of $\Sigma_i \alpha_i \vec{k}_{di}$ that best fits the measured data $\vec{m}$:

$$(\Sigma_i \alpha_i \vec{k}_{di} - \vec{m})^2 \rightarrow \min$$

The complex coefficients $\alpha_i$ can be found by solving the following real-valued linear system:

$$\begin{bmatrix} R_{K\times K} - I_{K\times K} & I_{K\times K} - R_{K\times K} \\ I_{K\times K} + R_{K\times K} & R_{K\times K} - I_{K\times K} \end{bmatrix} \begin{bmatrix} R(\alpha_1) \\ \vdots \\ R(\alpha_K) \\ T(\alpha_1) \\ \vdots \\ T(\alpha_K) \end{bmatrix} = \begin{bmatrix} A_{K\times 1} + B_{K\times 1} \\ A_{K\times 1} - B_{K\times 1} \end{bmatrix}$$

where the matrices, R, I, and the vectors A, B are defined as follows:

$$R_{i,j}=R(\vec{k}_{di}^* \cdot \vec{k}_{dj})$$

$$I_{i,j}=T(\vec{k}_{di}^* \cdot \vec{k}_{dj})$$

$$A_i=R(\vec{m}^* \cdot \vec{k}_{di})$$

$$B_i=T(\vec{m}^* \cdot \vec{k}_{di}).$$

Here, R(a), T(a), and a* are respectively the real part, imaginary part, and complex conjugate of the complex a.

Step 3 Details

The linear combination found in Step 2 can be used to add k-space data from the patient motion library to acquired matching lines by the following linear combination:

$$\vec{m}_i^j = \Sigma_{p=1}^K \alpha_p \vec{k}_{dp,i}^j, i \in [1,N] \cap i (\text{not} \in)[l_1, l_2, \ldots l_M],$$
$$j=1,\ldots,C.$$

An alternate approach accounts for the lines in the $d_1-1$, $d_2-1, \ldots d_K-1$ patient motion library datasets also have similar contributions as the lines in the $d_1, d_2, \ldots d_K$. Also, the closeness in time a given dataset is acquired relative to the matching lines can be accounted for. For example, the line $l_{M+1}$ in dataset $d_1$ is acquired immediately after the matching lines and can be given more weight in the combination than the $l_{M+1}$-th line in dataset $d_1-1$. One implementation of such a method can be expressed by:

$$\vec{m}_{li}^j = \sum_{p=1}^K \alpha_p \left( w_i^1 \vec{k}_{dp-1,li}^j + w_i^2 \vec{k}_{dp,li}^j \right),$$

$$i = M+1, M+2, \ldots N, j = 1, \ldots, C$$

-continued $$w_i^1 = \frac{i-M}{N-M+1}, w_i^2 = \frac{N-i+1}{N-M+1}$$

By the methods described above, planar images 320 constructed from planar k-space data 310 can be updated by replacing a corresponding radial line in previously acquired radial k-space data where the tracking data 220 is acquired along a single radial line in k-space. In this way, the reconstructed planar image is comprised of "old" radial lines and one new radial line. This allows the immediate generation of a partially updated planar image 320, as opposed to waiting for re-acquisition of all radial lines.

It is possible that a patient 100 can move in such a manner that a sufficiently good match between tracking data 220 and reference data 200 cannot be found. One example of how to address this can be to extrapolate reference data 200 to attempt to improve the match between tracking data 220 and reference data 200. For example, if reference data 200 captured normal breathing but during the time of interest patient 100 took a very deep breath, reference data 200 can be digitally extrapolated to attempt to match tracking data 220. The extrapolation can be based on a velocity of the changing shape of the patient anatomy. For example, being based on the velocity of lung expansion measured by the tracking data 220. If the match is found to be improved or sufficient, the extrapolated reference data can be added to the patient motion library.

Tracking (or partial volumetric) data can be represented by k-space vectors that correspond to a k-space representation of the tracking or partial volumetric data 210 acquired when imaging patient 100. These k-space vectors can be complex quantities with a real and an imaginary component. Alternatively stated, the k-space vectors can have a magnitude and a phase angle. If the patient anatomy undergoes a translation or rotation, the magnitude of the k-space vector representing a specific location of the patient anatomy does not change. What can change is the ratio of the real to the imaginary part of the vector, as represented by the phase angle. In some implementations, the change in phase angle contained in each coordinate or voxel of the tracking 220 or partial volumetric data 210 can be determined by subtracting phase angle measurements corresponding to tracking or partial volumetric data 210 that were acquired at different times. The determined change in phase angle can be related to a corresponding change in the position or orientation of the patient anatomy.

This method can be used to better match the acquired k-space data (for patient anatomy that may have shifted or rotated) to pre-existing k-space data. For example, there can be k-space data, including the reference 200, partial volumetric 210, or tracking 220 data, corresponding to the patient anatomy. Knowing that the patient anatomy can shift (e.g. linear translation), rotate, or both, while still retaining essentially the same physical shape, changes to any of the acquired k-space data can be applied to determine if a shift or rotation has occurred. Specifically, scaling factors or rotations can be applied to the k-space data that represent a shift or rotation of the patient anatomy. The k-space scaling factor can be proportional to a linear shift in Cartesian space. The rotation in k-space can be proportional to the rotation in Cartesian space. When the applied changes to the k-space data improve the matching of the k-space data to the known k-space data (e.g. reference 200, partial volumetric 210, tracking 220 data), then the patient motion phase can be determined even though the k-space data was changed by movement of the patient anatomy. In this way, some matching or reconstructions can occur by only varying the rotations or shifts in the k-space data, without having to reconstruct an entirely new patient motion state that may actually be the same as one already in the patient motion library. This can speed acquisition and matching when the patient anatomy moves or rotates, but does not otherwise deform.

Figure 6:
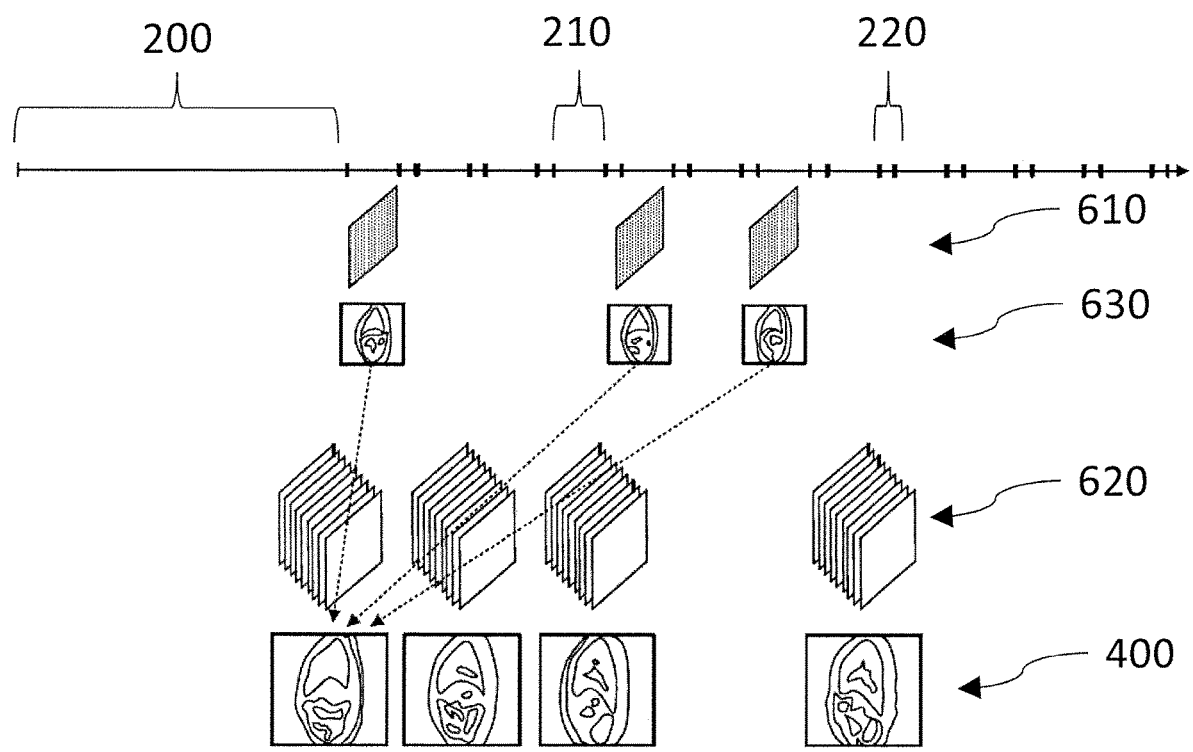
FIG. 6 is a diagram illustrating an example of a manner of combining partial volumetric data sets to form more full volumetric data sets.

FIG. 6 is a diagram illustrating slices of partial volumetric data 610 assembled to form volumetric data sets 620. A volumetric image of patient anatomy can be constructed that represents a particular motion state 630 from the acquired partial volumetric data 210 and acquired tracking data 220. Examples of particular motion states 630 are shown by the anatomical images in FIG. 6. The partial volumetric data 210 can be acquired, for example, as a series of slices 610 or planes in 3-D Cartesian k-space or as a collection of planar image data. Partial volumetric data 210, in addition to including planes in k-space, can correspond to any number of planes that intersect the patient anatomy. During a period of acquisition of partial volumetric data 210, one or more slices 610 (whether in image planes or k-space data) can be acquired.

The slices in Cartesian k-space can be acquired in several ways. One, the MRI system can excite only the desired planar region. This can allow acquisition of data with the knowledge that it relates only to that planar region. A second exemplary method can be to excite an entire patient volume and acquire only a specific partition of k-space data or plane through the patient 100.

The temporal proximity of the partial volumetric data 210 to a particular acquisition of tracking data 220 can allow the partial volumetric data 210 to be representative of the motion state corresponding to the tracking data 220. As shown by the arrows, the partial volumetric data 210 can then be binned according to the particular motion state 630. A sorting algorithm can be implemented to group or bin the partial volumetric data 210 into the appropriate motion state 400. As shown in FIG. 6, other than a beginning or ending acquisition, each acquisition of partial volumetric data 210 is bracketed by two acquisitions of tracking data 220. Partial volumetric data 210 can then be correlated with either tracking data 220 by virtue of their temporal proximity. Each of the two sets of tracking data 220 corresponding to the two acquisitions can be cross-correlated with clustered reference data 200. In some implementations, the average cross-correlation coefficient in each cluster can be used as a weighting factor. Partial volumetric data 210 can then be accumulated into the two bins corresponding to the motion states for the two clusters which have the largest weights. The accumulation can also be weighted by weighting factors (or correlation coefficients) for those motion states. As one example, say the tracking data 220 acquired at a particular time had a CC of 0.8 with motion phase 2, a CC of 0.3 with motion phase 5, and a CC of 0.1 with motion phase 8. Then, in this example, then the partial volumetric data 210 can be binned with motion phase 2 and given a weight of 0.8 and also binned with motion phase 5 with a weight of 0.3. In other implementations, any number of bins can receive the partial volumetric data 210 according to the weighting. For example, only one bin (corresponding to the highest weighting) can receive the partial volumetric data 210. In another implementation, all bins can receive the partial volumetric data 210, weighted accordingly.

Partial volumetric data 210 can be acquired according to a sequence of k-space regions similar to those for acquiring planar k-space data described above. After acquisition has begun, to avoid re-acquiring data for portions of k-space that have already been acquired for a particular motion state 400, the partial volumetric data 210 can be acquired for a k-space region that has not already been acquired. The selection of which k-space regions to acquire can be based on a continuously updated list of regions to be acquired. After a k-space region is acquired from the sequence, that k-space region can be removed from the list. In one implementation, a k-space scanning sequence can be pre-defined and executed. As partial volumetric data 210 is acquired and binned into motion states, the k-space scanning sequence can be updated to only, or preferentially, acquire partial volumetric data 210 corresponding to the motion states that have not been sufficiently imaged or have been imaged the least number of times. As one example, if there are three motion states and motion states 1 and 2 have been imaged 10 times and motion state 3 has only been imaged five times, then the acquisition of partial volumetric data 210 can be triggered only when the tracking data 220 confirms that the patient anatomy is in motion state 3.

In one implementation, if a sufficient quantity of partial volumetric data 210 was acquired such that a planar image can be constructed from it, then the tracking data 220 can be replaced by this subset of the partial volumetric data 210. In this way, the tracking data 220 can be extracted from the volumetric data, and then used as described above to correlate the partial volumetric data 210 with a motion state.

Similar to the fast acquisition of planar data described above, if partial (or complete) volumetric data is available from an earlier point in time, that data can be combined with the instantly acquired partial volumetric data 210. For example, if there is a complete set of volumetric data for a motion phase, a region of earlier partial volumetric data 210 can be replaced with the newly acquired partial volumetric data 210. The updated complete set of volumetric data can be used to generate an updated volumetric image.

Figure 7:
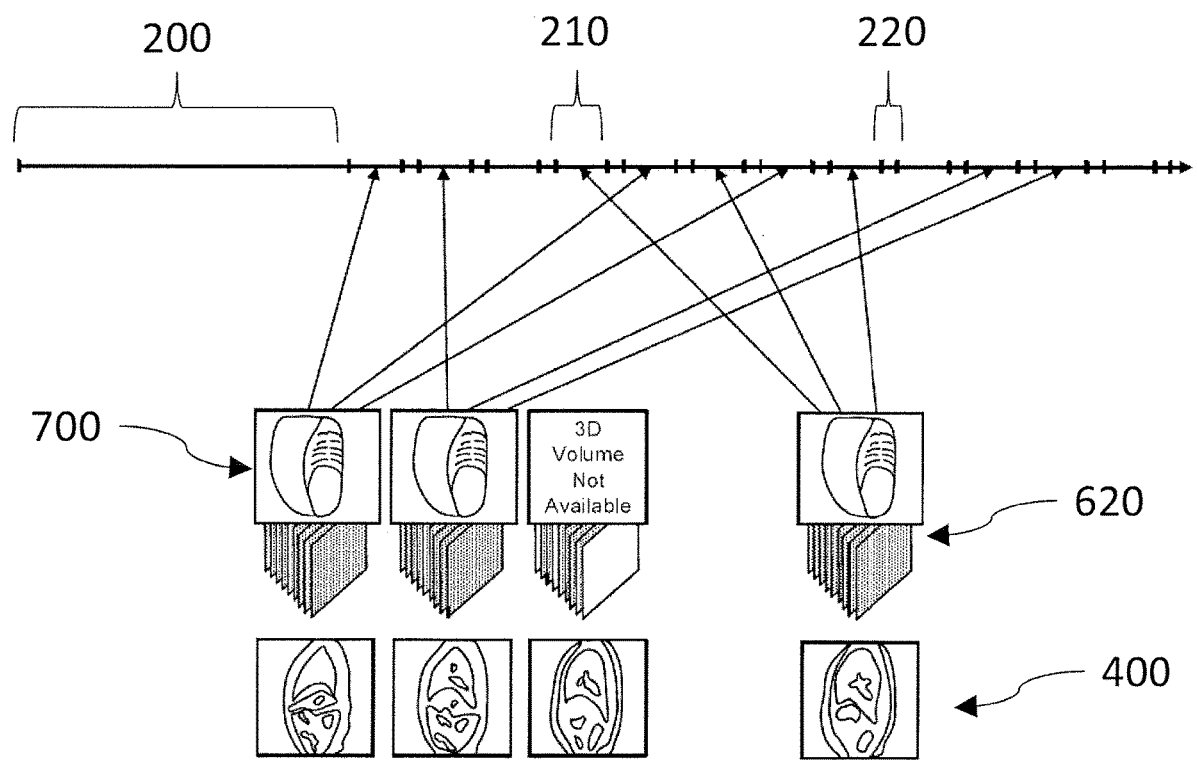
FIG. 7 is a diagram illustrating an exemplary manner of construction of a time-resolved volumetric image sequence.

FIG. 7 is a diagram illustrating the construction of a time-resolved volumetric image sequence. Reconstruction of patient volumes can be performed with accumulated partial volumetric data 210. As described above, this can be done by adding, based on the determined motion state, partial volumetric data 210 acquired during one of the motion states to a volumetric data set 620 corresponding to one of the motion states 400. A volumetric image 700 can be constructed from a complete or nearly complete set of partial volumetric data 210 through a 3-D Fast Fourier Transform (FFT). If the FFT is performed on a complete cluster, the reconstructed volumetric image 700 will be at the resolution defined by the k-space terms. With an incomplete 3-D volumetric dataset, either no image will be available (as shown for one dataset in FIG. 7) or the image will suffer distortions relative to the ideal complete volumetric image. The volumetric images 700 can then be combined to generate a time-resolved volumetric image sequence, as generally shown by the arrows in FIG. 7.

Figure 8:
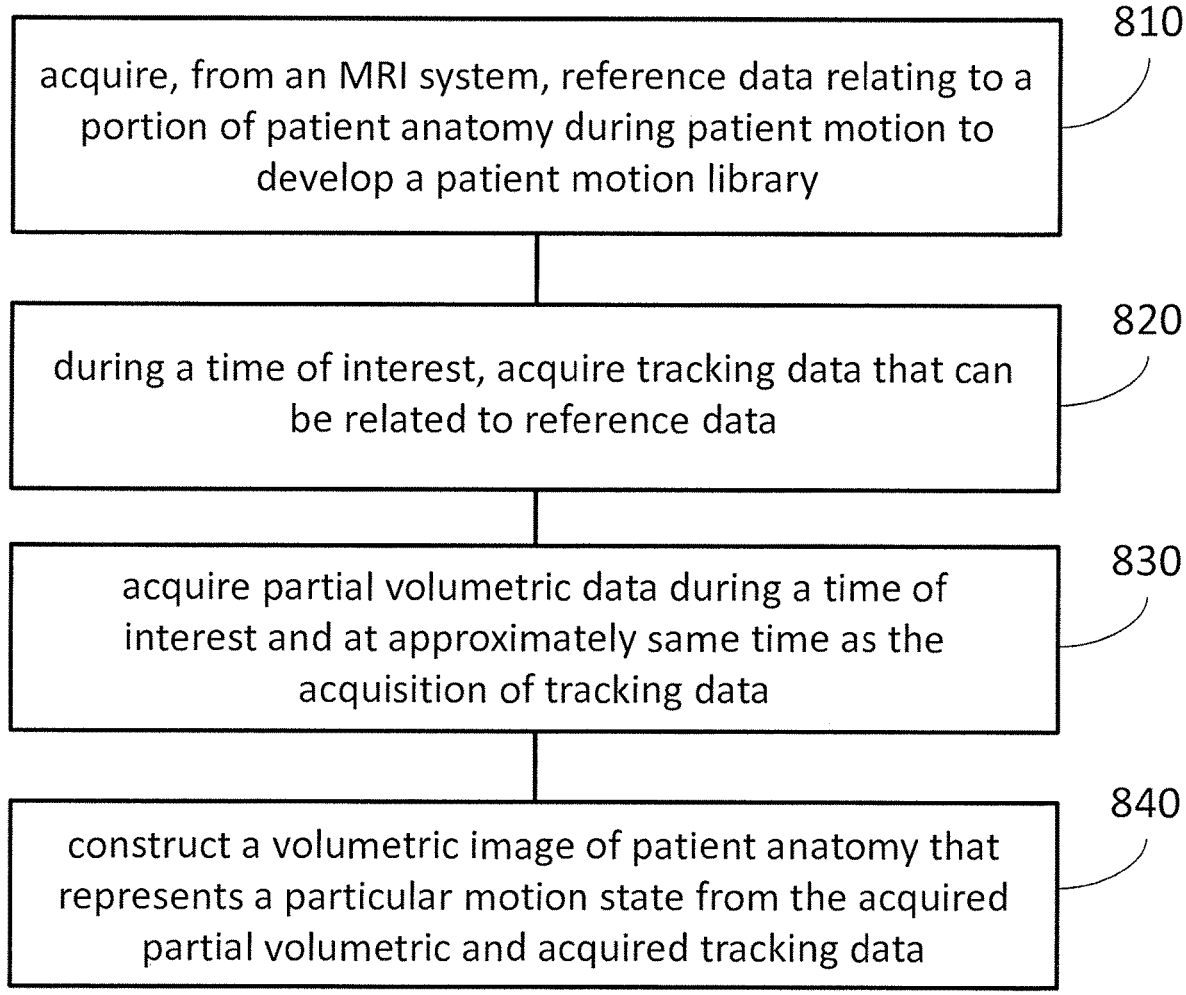
FIG. 8 is a process flow diagram illustrating an example of a method for the construction of volumetric images of patient anatomy.

FIG. 8 is a process flow diagram for the construction of a volumetric image 700 of patient anatomy. At 810, reference data relating to a portion of a patient anatomy during patient motion can be acquired from an MRI system to develop a patient motion library. At 820, tracking data, that can be related to the reference data, can be acquired during a time of interest. At 830, partial volumetric data can be acquired during the time of interest and at approximately the same time as the acquisition of the tracking data. At 840, a volumetric image of patient anatomy that represents a particular motion state can be constructed from the acquired partial volumetric data and acquired tracking data. Modifications of these steps may be made as described herein and further steps may be added, for example, a plurality of volumetric images may be constructed and then combined to generate a time-resolved volumetric image sequence.

Figure 9:
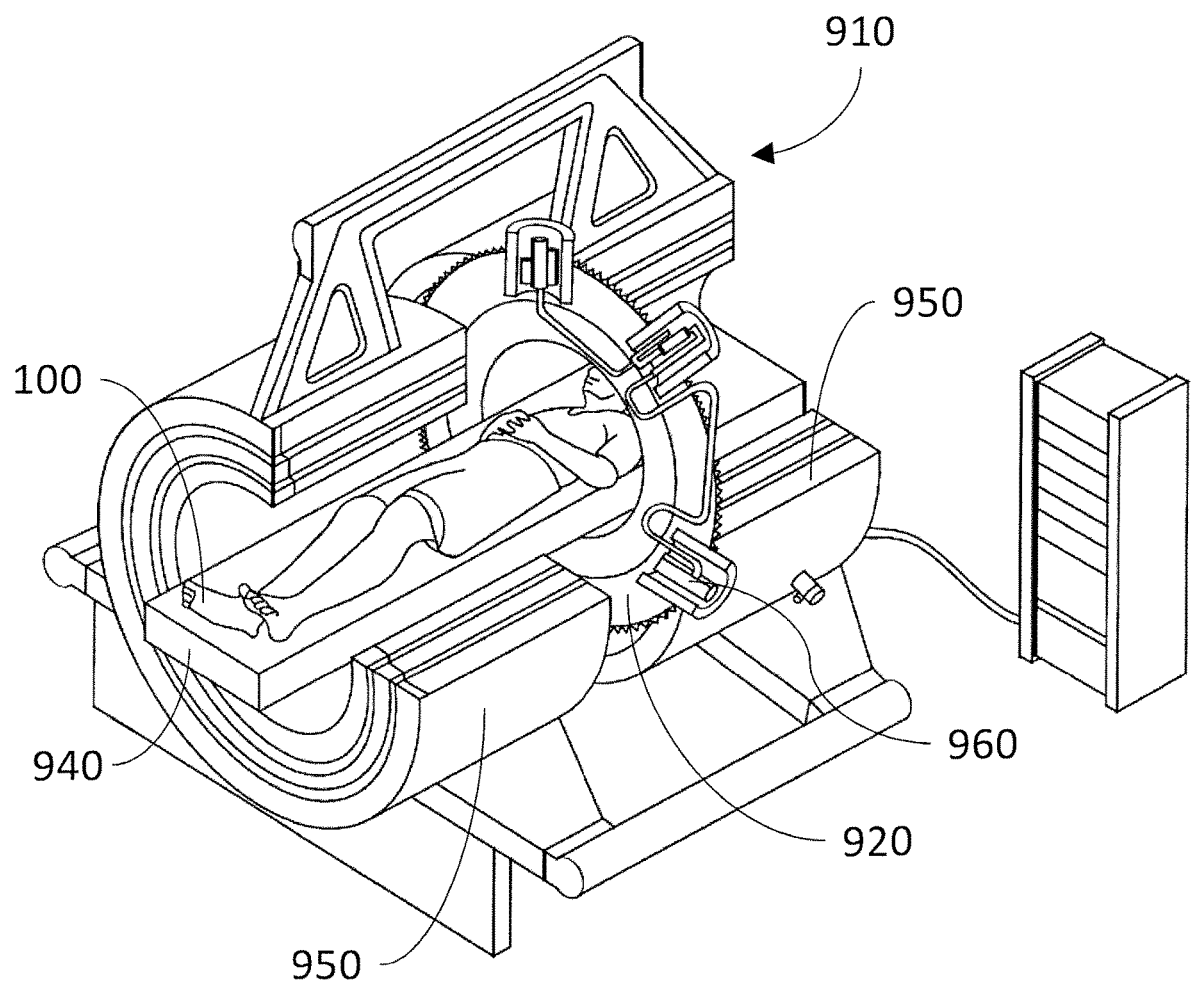
FIG. 9 is a diagram illustrating an example of a magnetic resonance imaging system used in conjunction with radiotherapy consistent with certain implementations of the present disclosure.

FIG. 9 is a diagram illustrating a magnetic resonance imaging system 910 including, among other things, a gantry 920 surrounding patient 100 lying on couch 940. The main magnetic field of MRI 910 is generated by split main magnet coils 950 in this example (although other magnet configurations may be used). MRI 910 is integrated with radiotherapy device 960 for the delivery of MRI-guided radiation therapy treatment. In the particular example depicted in FIG. 9, treatment is being delivered by a linear accelerator, which has been broken down into subcomponents contained within three separate shielding containers around gantry 920. However, the present disclosure contemplates that any type of radiotherapy device capable of delivering a beam of radiation to patient 100 may be used, for example, radioisotope therapy, proton therapy, heavy ion therapy, etc.

Images and time-resolved volumetric imaging sequences constructed as described herein can be used to enhance the delivery of radiation therapy. For example, radiation treatment can be delivered to a patient 100 based on tracking data 220. As discussed above, tracking data 220 can be, for example, planar image data that can be reconstructed into a planar image 320 during patient treatment. Planar images 320 can provide information as to the location of patient anatomy relative to the beam of radiation from radiotherapy device 960. The radiation therapy beam may then be varied based on knowing the nearly instantaneous state and location of the patient anatomy. For example, the output of radiotherapy device 960 can be gated, altered, or the like, based on received tracking data 220 and/or reconstructed images of patient anatomy.

Time-resolved volumetric image sequences can provide detailed information on the location of patient anatomy during radiation therapy and can therefore be used after treatment to verify how well the treatment was delivered, for example, by calculating a delivered dose distribution and comparing it to the prescribed dose distribution.

In addition, models that predict the motion of patient anatomy can be better trained by comparing tracking data received during treatment with the measured volumetric data. For example, if a particular set of tracking data is a good predictor of patient motion, then that data can be preferentially used when delivering radiotherapy treatment.

Furthermore, with sufficiently well-correlated tracking data and volumetric data, the achievability of a treatment plan can be predicted based only on the reference data 200. This can permit session-by-session updates to the treatment plan based on the current patient condition, without having to perform volumetric image reconstruction.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as would a non-transient solid-state memory or a magnetic hard drive or any equivalent storage medium. The machine-readable medium can alternatively or additionally store such machine instructions in a transient manner, for example, as would a processor cache or other random access memory associated with one or more physical processor cores.

To provide for interaction with a user, one or more aspects or features of the subject matter described herein can be implemented on a computer having a display device, such as a cathode ray tube (CRT) or a liquid crystal display (LCD) or a light emitting diode (LED) monitor for displaying information to the user and a keyboard and a pointing device, for example, a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on,"

above and in the claims is intended to mean, "based at least in part on," such that an unrecited feature or element is also permissible.

The subject matter described herein can be embodied in systems, apparatus, methods, computer software and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A computer program product comprising a non-transitory machine-readable medium storing instructions which, when executed by at least one processor forming at least part of a computing system, result in operations comprising:
   acquiring from a magnetic resonance imaging system (MRI), over a first period, reference data relating to a portion of a patient anatomy during patient motion to develop a patient motion library;
   during a time of interest, different from the first period, acquiring tracking data that is related to the reference data;
   acquiring partial volumetric data during the time of interest and at approximately the same time as the acquisition of the tracking data; and
   constructing a volumetric image of patient anatomy that represents a particular motion state from the acquired partial volumetric data and acquired tracking data.

2. The computer program product of claim 1, wherein a plurality of volumetric images are constructed and combined to generate a time-resolved volumetric image sequence.

3. The computer program product of claim 1, further comprising adding at least some of the tracking data or the partial volumetric data to the patient motion library.

4. The computer program product of claim 1, wherein the tracking data is planar k-space data.

5. The computer program product of claim 1, wherein the tracking data is three-dimensional k-space data.

6. The computer program product of claim 1, wherein the tracking data and the partial volumetric data are acquired in direct sequence.

7. The computer program product of claim 1, further comprising delivering radiation treatment to a patient based at least on the tracking data.

8. The computer program product of claim 1, wherein the partial volumetric data is acquired according to a predefined sequence of k-space regions, and wherein the partial volumetric data corresponds to a k-space region from the predefined sequence that has not already been acquired.

9. The computer program product of claim 1, the constructing comprising:
   partitioning the patient motion library into a plurality of motion states, each of the motion states corresponding to a portion of the patient motion;
   determining the motion state corresponding to the tracking data by finding a closest match between the tracking data and the reference data; and
   adding, based on the determined motion state, the partial volumetric data acquired during one of the plurality of motion states to a volumetric data set corresponding to the one of the plurality of motion states, the constructed volumetric image comprising a complete set of partial volumetric data.

10. The computer program product of claim 1, wherein the reference data is an integrated projection through the portion of the patient anatomy.

11. The computer program product of claim 1, wherein the partial volumetric data is a plurality of planar data corresponding to a plurality of planes in the portion of the patient anatomy.

12. The computer program product of claim 1, wherein the tracking data corresponds to a subset of radial k-space data that is used to reconstruct the portion of the patient anatomy corresponding to a closest match of the tracking data with the reference data.

13. The computer program product of claim 1, the acquiring of the tracking data further comprising replacing a corresponding radial line in previously acquired radial k-space data where the tracking data is acquired along a single radial line in k-space.

14. The computer program product of claim 1, the relating of the tracking data to the reference data comprising deforming, by digital interpolation, extrapolation, or translation, of the reference data to improve a goodness-of-fit metric that describes a quality of the relating of the tracking data to the reference data.

15. The computer program product of claim 14, wherein the deforming is further based on a velocity of patient motion measured from the tracking data.

16. The computer program product of claim 1, the operations further comprising:
   controlling a radiotherapy device to deliver radiation treatment to a patient,
   wherein the acquiring of the reference data occurs before delivering radiation treatment to the patient.

17. The computer program product of claim 1, the operations further comprising:
   controlling a radiotherapy device to deliver radiation treatment to a patient,
   wherein the acquiring of the reference data occurs after delivering radiation treatment to the patient.

18. The computer program product of claim 1, wherein the reference data is k-space data.

19. The computer program product of claim 1, wherein the reference data is planar image data.

20. The computer program product of claim 1, wherein the partial volumetric data is k-space data.

21. The computer program product of claim 1, wherein the partial volumetric data is planar image data.

22. The computer program product of claim 1, further comprising correlating the partial volumetric data with the tracking data.

23. The computer program product of claim 1, the operations further comprising:
   controlling a radiotherapy device to deliver radiation treatment to a patient,
   wherein the time of interest is during delivery of radiation treatment to a patient.

24. The computer program product of claim 1, the operations further comprising:

controlling the MRI to acquire MRI data during a period of diagnostic observation,
wherein the time of interest is during the period of diagnostic observation.

25. The computer program product of claim 1, wherein the partial volumetric data is acquired immediately after the acquiring of the tracking data.

26. The computer program product of claim 1, wherein the acquiring of tracking data and partial volumetric data is continuous and alternating between the acquisition of tracking data and partial volumetric data.

27. The computer program product of claim 1, wherein the reference data utilized to develop the patient motion library is acquired before or after the acquisition of the partial volumetric data.

28. A method for implementation by at least one programmable processor, the method comprising:
    acquiring from a magnetic resonance imaging system (MRI), over a first period, reference data relating to a portion of a patient anatomy during patient motion to develop a patient motion library;
    during a time of interest, different from the first period, acquiring tracking data that is related to the reference data;
    acquiring partial volumetric data during the time of interest and at approximately the same time as the acquisition of the tracking data; and
    constructing a volumetric image of patient anatomy that represents a particular motion state from the acquired partial volumetric data and acquired tracking data.

29. The method of claim 28, wherein the reference data utilized to develop the patient motion library is acquired before or after the acquisition of the partial volumetric data.

30. A system comprising:
    at least one processor; and
    a non-transient machine-readable medium storing instructions which, when executed by the at least one processor, cause the at least one processor to perform operations comprising:
        acquiring from a magnetic resonance imaging system (MRI), over a first period, reference data relating to a portion of a patient anatomy during patient motion to develop a patient motion library;
        during a time of interest, different from the first period, acquiring tracking data that is related to the reference data;
        acquiring partial volumetric data during the time of interest and at approximately the same time as the acquisition of the tracking data; and
        constructing a volumetric image of patient anatomy that represents a particular motion state from the acquired partial volumetric data and acquired tracking data.

31. The system of claim 30, wherein the reference data utilized to develop the patient motion library is acquired before or after the acquisition of the partial volumetric data.

* * * * *